(12) United States Patent
Liao et al.

(10) Patent No.: US 11,045,401 B2
(45) Date of Patent: Jun. 29, 2021

(54) PARTIAL MELT CO-CRYSTALLIZATION COMPOSITIONS

(71) Applicant: Heartland Consumer Products, LLC, Carmel, IN (US)

(72) Inventors: Shyhyuan Liao, West Windsor, NJ (US); Joseph R. Panarisi, Manalapan, NJ (US); Steven J. Catani, Athens, GA (US)

(73) Assignee: Heartland Consumer Products LLC, Carmel, IN (US)

( * ) Notice: Subject to any disclaimer, the term of this patent is extended or adjusted under 35 U.S.C. 154(b) by 0 days.

(21) Appl. No.: 14/312,842

(22) Filed: Jun. 24, 2014

(65) Prior Publication Data

US 2015/0030547 A1    Jan. 29, 2015

Related U.S. Application Data

(60) Provisional application No. 61/857,934, filed on Jul. 24, 2013.

(51) Int. Cl.
| | | |
|---|---|---|
| *A61K 8/34* | (2006.01) | |
| *A61Q 11/00* | (2006.01) | |
| *A23L 27/00* | (2016.01) | |
| *A23L 27/10* | (2016.01) | |
| *A23L 27/30* | (2016.01) | |
| *A23P 10/10* | (2016.01) | |
| *A61K 9/14* | (2006.01) | |
| *A61K 8/02* | (2006.01) | |
| *A23P 10/40* | (2016.01) | |

(52) U.S. Cl.
CPC .............. *A61K 8/345* (2013.01); *A23L 27/10* (2016.08); *A23L 27/30* (2016.08); *A23L 27/34* (2016.08); *A23L 27/86* (2016.08); *A23P 10/40* (2016.08); *A61K 8/022* (2013.01); *A61K 9/145* (2013.01); *A61Q 11/00* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,886,677 A | 12/1989 | Kondou | |
| 5,080,916 A * | 1/1992 | Kondou | .................. A23L 27/34 426/548 |
| 5,723,106 A * | 3/1998 | Buch | ........................ A61K 8/34 424/49 |
| 5,962,678 A * | 10/1999 | Payzant | .................. A23L 27/36 536/127 |
| 6,030,820 A | 2/2000 | Morioka et al. | |
| 6,461,659 B1 * | 10/2002 | Zhou | ....................... A23L 27/36 426/103 |
| 6,475,552 B1 | 11/2002 | Shah et al. | |
| 6,559,302 B1 | 5/2003 | Shah et al. | |
| 6,875,460 B2 | 4/2005 | Cunningham et al. | |
| 8,277,862 B2 | 10/2012 | Lee et al. | |
| 2006/0073255 A1 | 4/2006 | Catani et al. | |
| 2006/0263423 A1 | 11/2006 | Norman et al. | |
| 2007/0026121 A1 | 2/2007 | Benedict et al. | |
| 2007/0116828 A1 * | 5/2007 | Prakash | .................. A23L 27/36 426/548 |
| 2009/0004355 A1 | 1/2009 | Catani | |
| 2009/0011104 A1 | 1/2009 | Catani et al. | |
| 2009/0104326 A1 * | 4/2009 | Catani | ..................... A23L 27/34 426/472 |
| 2010/0222311 A1 | 9/2010 | Thommes et al. | |
| 2012/0157416 A1 | 6/2012 | Kumiega | |
| 2016/0165939 A1 * | 6/2016 | Berry | ....................... A23L 27/72 426/103 |

FOREIGN PATENT DOCUMENTS

| | | | | |
|---|---|---|---|---|
| WO | WO 2011026003 A2 * | 3/2011 | ........... A23G 3/0021 |
| WO | WO-2012001547 A1 * | 1/2012 | ............... A23G 4/06 |

OTHER PUBLICATIONS

Hubert Schiweck, et al. Sugar Alcohols. From Ullmann's Encyclopedia of Industrial Chemistry. Weinheim: Wiley-VCH, 2012, pp. 1-37.*
Definition of "Solid solution" from Encyclopedia Britannica. Downloaded Sep. 7, 2016 from: https://www.britannica.com/science/solid-solution, 1 printed page.*
"Melting and dissolving", online document posted by the Victoria State Government, downloaded Jun. 15, 2017 from http://www.education.vic.gov.au/school/teachers/teachingresources/discipline/science/continuum/Pages/meltdissolve.aspx.*
Hong-xun Hao, Bao-hong Hou, Jing-kang Wang, and Mei-jing Zhang. Solubility of Erythritol in Different Solvents. J. Chem. Eng. Data 2005, 50, 1454-1456 (Year: 2005).*
International Search Report and Written Opinion, PCT/US14/43769, McNeil Nutritionals, Inc., dated Oct. 29, 2017, 9 pgs.
European Search Report, EP Patent No. 14742039.2, McNeil Nutritionals, Inc., dated Dec. 11, 2017, 4 pgs.
Patent Examination Report No. 1; Australian Patent Office; dated May 4, 2017, 2 pgs.

* cited by examiner

*Primary Examiner* — Michael P Cohen
(74) *Attorney, Agent, or Firm* — Taft Stettinius & Hollister LLP; Joseph M. Bennett-Paris (57) ABSTRACT

A co-crystallization composition containing erythritol and an active; a method of making the co-crystallization composition; and a method of using the co-crystallization composition are disclosed.

5 Claims, 5 Drawing Sheets

Co-crystallized Erythritol/Malic Acid vs. Dry Blended Erythritol/Malic Acid

| Panelist | Samples & Codes | | | | Correct? | Comments |
|---|---|---|---|---|---|---|
| | Co-crystalized | | Dry blend only | | | |
| | 396 | 427 | 174 | 805 | | |
| CA |  | X |  |  | N | less sour |
| SW |  |  | X |  | N | less sweet |
| CS |  |  | X |  | Y | slightly sweet |
| JW |  | X |  |  | Y | less sour |
| JSP | X |  |  |  | Y | less sour |
| CA | X |  |  |  | Y | less sour, more sweet |
| MA |  |  |  | X | N | more tart |
| CB |  |  |  | X | Y | metallic, more acidic |
| MH |  |  | X |  | Y | more acidic |
| AH |  |  |  | X | N | more tart |
| JAS |  |  |  | X | N | less sugar taste |
| JS | X |  |  |  | Y | less acidic |
| MC |  |  | X |  | Y | more sour |
| JP |  | X |  |  | Y | longer linger |
| SB |  |  |  | X | Y | more sour |

Conclusions
1) 10 panelists of 15 correctly picked the odd sample. Difference significant (for significance would need min. 9 correct answers).
2) Those who correctly chose sample overwhelmingly commented co-crystalized less sour or dry blend more sour as reason for choice.
3) Those who chose incorrectly frequently noted co-crystalized sample less sour or dry blend sample more sour.

| Ingredient | Composition | Triangle Test Blends (g) | |
|---|---|---|---|
| | | Co-crystalized | Dry blend |
| Co-crystalized erythritol/malic acid | 60.8% malic acid/39.2% erythritol | 12.0 | -- |
| Erythritol | 100% erythritol | 188.0 | 192.7 |
| Malic acid | 100% malic acid | -- | 7.3 |
| | Total | 200.0 | 200.0 |

Triangle Test Method for Co-crystalized vs. Dry Blended Erythritol/Malic Acid
1) Triangle test blends blended in turbula for 5 minutes
2) Sample size 0.3g
3) Samples evaluated by depositing entire sample on tongue
4) Evaluators rinsed mouth with water before and between samples
5) Samples presented in random order
6) Odd sample randomly either co-crystalized or dry blend
7) Panelist chose odd sample and gave reason for choice

*FIG. 2*

| ONLY CHANGE GREEN CELLS | | | | | | | Date | 2/14/2013 |
|---|---|---|---|---|---|---|---|---|
| | | | | | | | | |
| Name: | | | | Date: | 2/14/2013 | | Ballot Number | |
| | | | | | | | 10 | |
| Please rinse your mouth before starting and between samples. CONSUME ENTIRE SAMPLE. | | | | | | | | |
| Circle the sample that is different (if you are not sure make a guess): | | | | | | | | |
| You must give a reason for your choice. | | | | | | | | |
| | | 805 | 174 | 427 | | | | |
| | | | | | | | | |
| Reason for difference: | | | | | | | | |
| | | | | | | | | |
| | | | | | | | | |
| Name: | | | | Date: | 2/14/2013 | | Ballot Number | |
| | | | | | | | 15 | |
| Please rinse your mouth before starting and between samples. CONSUME ENTIRE SAMPLE. | | | | | | | | |
| Circle the sample that is different (if you are not sure make a guess): | | | | | | | | |
| You must give a reason for your choice. | | | | | | | | |
| | | 396 | 427 | 174 | | | | |
| | | | | | | | | |
| Reason for difference: | | | | | | | | |
| | | | | | | | | |
| | | | | | | | | |
| Name: | | | | Date: | 2/14/2013 | | Ballot Number | |
| | | | | | | | 9 | |
| Please rinse your mouth before starting and between samples. CONSUME ENTIRE SAMPLE. | | | | | | | | |
| Circle the sample that is different (if you are not sure make a guess): | | | | | | | | |
| You must give a reason for your choice. | | | | | | | | |
| | | 805 | 427 | 174 | | | | |
| | | | | | | | | |
| Reason for difference: | | | | | | | | |

*FIG. 3*

| Ballot # | sample presented first (far left) | sample presented second (middle) | sample presented third (far right) | | Ballot order | 20 | press F9 key to scroll through randomized order of ballots to use | |
|---|---|---|---|---|---|---|---|---|
| 1 | 427 | 805 | 396 | | | | | |
| 2 | 427 | 396 | 805 | | | | | |
| 3 | 805 | 427 | 396 | | | | | |
| 4 | 805 | 396 | 427 | | | | | |
| 5 | 396 | 427 | 805 | | | | | |
| 6 | 396 | 805 | 427 | | | | | |
| 7 | 427 | 805 | 174 | | | | | |
| 8 | 427 | 174 | 805 | | | | | |
| 9 | 805 | 427 | 174 | | | | | |
| 10 | 805 | 174 | 427 | | | | | |
| 11 | 174 | 427 | 805 | | | | | |
| 12 | 174 | 805 | 427 | | | | | |
| 13 | 427 | 396 | 174 | | | | | |
| 14 | 427 | 174 | 396 | | | | | |
| 15 | 396 | 427 | 174 | | | | | |
| 16 | 396 | 174 | 427 | | | | | |
| 17 | 174 | 427 | 396 | | | | | |
| 18 | 174 | 396 | 427 | | | | | |
| 19 | 805 | 396 | 174 | | | | | |
| 20 | 805 | 174 | 396 | | | | | |
| 21 | 396 | 805 | 174 | | | | | |
| 22 | 396 | 174 | 805 | | | | | |
| 23 | 174 | 805 | 396 | | | | | |
| 24 | 174 | 396 | 805 | | | | | |

*FIG. 4*

SPI Polyols, Inc.

POLYOLS COMPARISON CHART

| Raw Material | % Relative Sweetness vs. Sucrose | Calorie Content (Kcal/g) | | | Laxation Threshold (g/day) | Solubility at 26°C (g/100g H₂O) | Heat of Solution (cal/g) | Melting Point (°C) | Degree of Hygroscopicity % ERH @ 20°C | Molecular Weight | GRAS USA | Canada |
|---|---|---|---|---|---|---|---|---|---|---|---|---|
| | | USA | Canada | Japan | | | | | | | | |
| Sorbitol | 60 | 2.6 | 2.6 | 3 | 50 | 235g | -26.5 | 99-101 | Medium | 182 | Yes | Yes* |
| Mannitol | 50 | 1.6 | 1.6 | 2 | 20 | 22g | -28.9 | 165-169 | Very Low | 182 | Food Additive | Yes* |
| HSH | 30-40 | 3** | 3 | 2.3-3.4 | 70-140 | soluble | n/a | n/a | Medium | HP+ | Yes† | Yes* |
| Maltitol Solution | 70-80 | 3** | 3 | 2.3-3.4 | 70-80 | soluble | n/a | n/a | Medium | HP+ | Yes† | Yes* |
| Maltitol | 90 | 2.1 | 3 | 2 | 100 | 175g | -5.5 | 144-147 | Low | 344 | Yes† | Yes* |
| Xylitol | 100 | 2.4 | 3 | 3 | 50 | 200g | -36.6 | 92-95 | High | 152.17 | Food Additive | Yes* |
| Lactitol Monohydrate | 30-40 | 2 | 2 | 2 | 20-50 | 140g | -13.9 | 95-101 | Low | 362.33 | Yes† | Yes* |
| Anhydrous Isomalt | 40 | 2 | 2 | 2 | 50 | 39g | -9.4 | 145-150 | Very Low | 344.32 | Yes† | Yes* |
| Erythritol | 60-70 | 0.2 | 2.6 | 0 | High | 61g | -42.9 | 119-123 | Very Low | 122 | Yes† | Pending |
| Glycerin | 55-75 | 4.3 | 4.3 | - | High | soluble | +16.0 | 17.8 | Medium | 99 | Yes | Yes |
| Polydextrose | 0 | 1 | 1 | 1 | 90 | 80g | +9.0 | 130 | High | <22,000 | Food Additive | Yes* |
| Sucrose | 100 | 4 | 4 | 4 | None | 185g | -4.3 | 160-186 | Low | 342 | Yes | Yes |
| Fructose | 117 | 4 | 4 | 4 | None | 400g | -8.0 | 102-105 | High | 180 | Yes | Yes |
| Maltose | 30 | 4 | 4 | 4 | None | 70g | -8.0 | 120-125 | Medium | 342 | Food | Food |

*Extended to Use in Unstandardized Food
**Based on solids
†Self-Affirmed GRAS

FIG. 5

PARTIAL MELT CO-CRYSTALLIZATION COMPOSITIONS

CROSS REFERENCE TO RELATED APPLICATIONS

This application claims priority from U.S. Provisional Application Ser. No. 61/857,934, filed Jul. 24, 2013, the contents of which are hereby incorporated by reference in their entirety.

FIELD OF THE INVENTION

The present invention relates to partial melt co-crystallization compositions that contain a crystallizable carrier and an active. The present invention also relates to a process for manufacturing the partial melt co-crystallization compositions and to methods of using the partial melt co-crystallization compositions in consumer products such as sweeteners and over the counter (OTC) pharmaceutical dosage forms.

BACKGROUND OF THE INVENTION

People often customize the taste of food and beverages by adding sweeteners thereto. Sweetening food or beverages with a tabletop sweetener alters its flavor and increases its appeal. Although this behavior is found in all cultures, it is especially prevalent in western cultures.

Personal taste creates considerable variability in the amount of sweetness that one person prefers in a given food or beverage versus another person. For example, the amount of sweetness incorporated into a foodstuff during commercial production may not be adequate to satisfy some consumers while other consumers may find the same amount of sweetness to be excessive. Moreover, consumers often desire to reduce their caloric intake for health or lifestyle reasons. There therefore exists a need for sweetener products that consumers may use that are consistent with their personal preferences and minimize additional caloric burden.

Tabletop sweeteners are the primary vehicle by which such taste customization is accomplished. Many types of sweeteners are used as tabletop sweeteners. These include simple sugars, e.g., sucrose, fructose, and ketose; complex sweeteners, e.g., honey, molasses, and agave nectar; and high intensity sweeteners, e.g., sucralose, saccharine, and aspartame. Tabletop sweeteners are presently available in many different forms, including, granular, cohesive non-free flowing compositions (e.g., cubes and tablets), and the like.

Sweeteners have also been added to pharmaceuticals in order to make them more palatable and to mask the unpleasant taste often associated them.

NECTRESSE™ Natural No Calorie Sweetener, McNeil Nutritionals, LLC,| Fort Washington, Pa., is a combination of deliciously sweet monk fruit extract blended with other natural sweeteners (erythritol, sugar and molasses) that has the sweet taste of sugar without all the calories.

*Siraitia grosvenorii* is an herbaceous perennial vine of the Cucurbitaceae (gourd) family, native to southern China and northern Thailand. The plant is cultivated for its fruit, whose extract is nearly 300 times sweeter than sugar and has been used in China as a natural low-calorie sweetener for cooling drinks, and in traditional Chinese medicine to treat diabetes and obesity.

The plant's fruit is often called in English language publications luo han guo.

Monk fruit is notable for its sweetness, which can be concentrated from its juice. The fruit contains 25 to 38% of various carbohydrates, mainly fructose and glucose. The sweetness of the fruit is increased by the mogrosides, a group of triterpene glycosides (saponins). The five different mogrosides are numbered from I to V; the main component is mogroside V, which is also known as esgoside. The fruit also contains vitamin C. The sweet taste of the fruit comes mainly from mogrosides, a group of triterpene glycosides that make up about 1% of the flesh of the fresh fruit. Through solvent extraction, a powder containing 80% mogrosides can be obtained, the main one being mogroside-5 (esgoside) Other similar agents in the fruit are siamenoside and neomogroside.

Monk fruit is most prized for its sweet fruits, which are used for medicinal purposes such as a cough home remedy and as a sweetener. The fruits are generally sold in dried form, and traditionally used in herbal tea or soup.

Erythritol

Erythritol is a natural, low calorie sweetener. It has a bright, sweet taste that is about 70% the sweetness of sucrose (cane sugar) on a weight basis. It is found in grapes and other fruits and can be produced in large quantities by fermentation from sugar. It contains less than 0.2 kcals per gram and provides the equivalent of a teaspoon of sugar for around 1.2 kcals. While the caloric content is not as low as high intensity sweeteners, it compares very favorable with sucrose (about 16 kcals/tsp), fructose (about 14 Kcal/tsp SES), and tagatose (about 6.6 kcals/tsp SES) for those seeking to reduce calories.

Erythritol, which is a 4-carbon polyol, and which is also known as 1,2,3,4-butanetetrol, meso-erythritol, erythrol, erythrite, paycite, antierythrite, and phycitol (ChemIDPlus, 2010), has a molecular formula of $C_4H_{10}O_4$ and a molecular weight of 122.12 daltons. The chemical structure of erythritol is given below.

Erythritol is heat stable, non-hygroscopic, and exists as a white, odorless crystal. A summary of the physical and chemical properties of erythritol is presented in Table 1 below.

TABLE 1

| Generic Name | Eryrithritol |
| --- | --- |
| Formal (IUPAC) Name | 1,2 3,4-butanetetrol |
| CAS Registry No. | 149-32-6 |
| Molecular formula | $C_4H_{10}O_4$ |
| Molecular Weight | 122.12 daltons |
| Melting Point | 118-120° C. |
| Boiling Point | 329-331° C. |
| Solubility in water | Soluble |
| Solubility in ethanol | Slight |
| Solubility in DMSO | Insoluble |
| Color | White |
| Odor | Odorless |
| Taste | Sweet |
| Form | Crystal |

*O'Laughlin Biotech Company GRAS Notification for Erythritol (2011).

Erythritol has well-known characteristics which can be utilized for its identification. Erythritol is known to be stable under heat, acid, and alkaline conditions. Erythritol is water soluble and is slightly soluble in alcohol.

Figure 5:
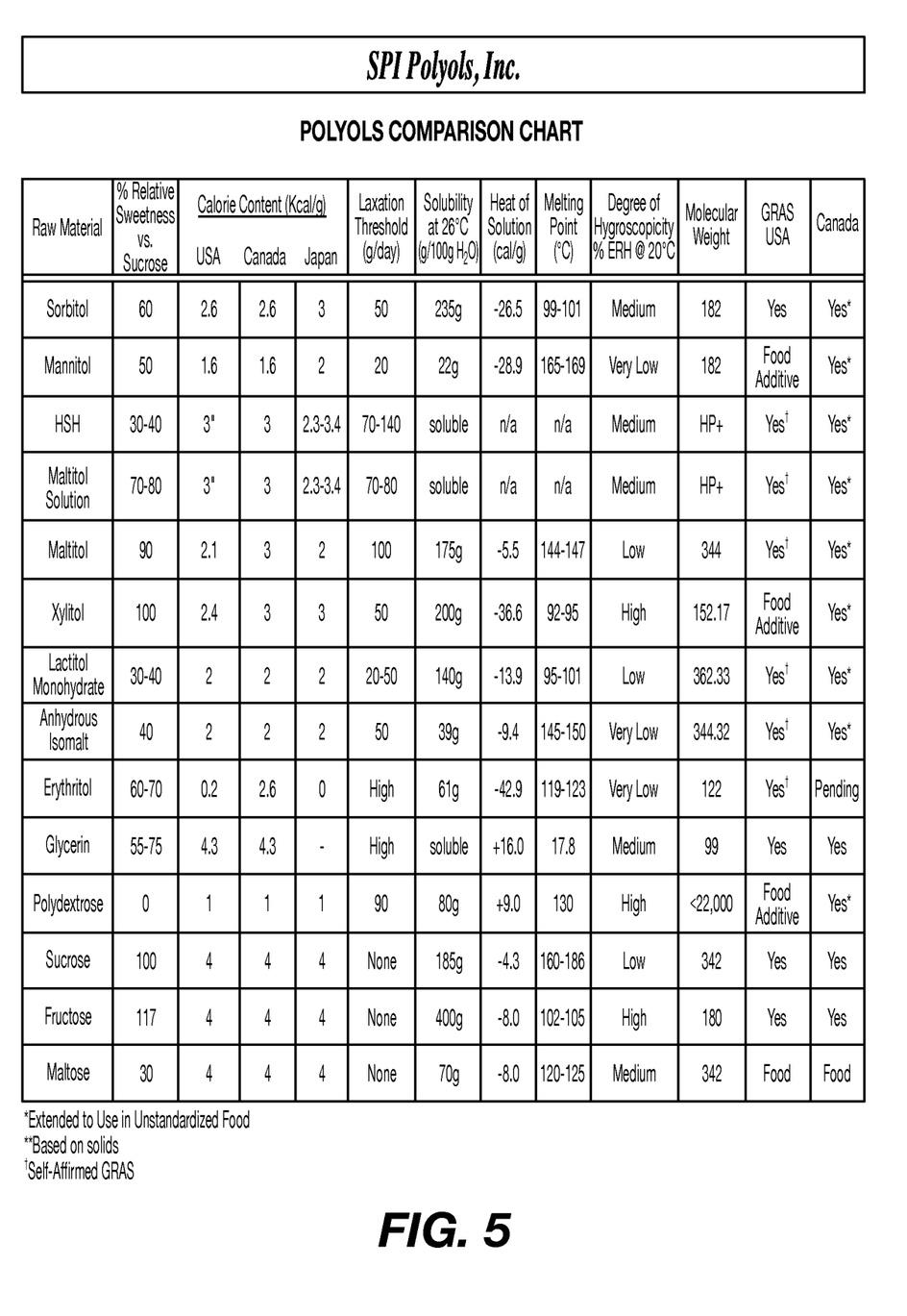
FIG. 5 is SPI Polyols, Inc. Polyols Comparison Chart.

Other food grade crystals that are water-soluble, crystalline and have melting points below 200° C. can be employed in accordance with the invention. For example, sorbitol (mp at 99° C.-101° C.); mannitol (mp at 165° C.-169° C.); maltitol (mp at 144° C.-147° C.), xylitol (mp at 92° C.-95° C.); polydextrose (mp at 130° C.); sucrose (mp at 160° C.-186° C.); maltose (mp at 120° C.-125° C.). Additional polyols that may be used in accordance with the invention are listed in SPI Polyols, Inc. Polyols Comparison Chart shown in FIG. 5.

While the sweet taste is pleasant, erythritol has a high negative heat of solution and provides a cooling sensation. Further, the sweet taste is very monochromatic and lacks the flavor complexity of many natural sweeteners. While erythritol's caloric burden is low, the above taste properties are not considered ideal.

Several strategies have been used to overcome erythritol's taste problems. One solution to the negative heat of solution has been to combine erythritol with a material having a positive heat of solution, e.g., fructo-oligosaccharides ("FOS"), inulin and glycerin. Unfortunately, these materials have shortcomings, e.g., inulin and FOS have a propensity to cause gas and bloating when consumed in moderate to large quantities.

Erythritol, which is absorbed into the bloodstream in the small intestine, for the most part is excreted unchanged in the urine. Because erythritol is normally absorbed before it enters the large intestine, it does not normally cause laxative effects as may be experienced after over-consumption of other sugar alcohols.

Erythritol is known to mask bitter and metallic tastes from certain high intensity sweeteners. A well-known example is extracts of the *Stevia Rebaudiana* plant. Although the components of the aqueous extracts of this plant, known as steviosides and rebaudiosides, are very sweet (180-300 times sweeter than sucrose), they have metallic and bitter notes. Previously disclosed formulas use small amounts of erythritol to mask the bitter notes in compositions where the primary sweetness is coming from *stevia*.

U.S. Published Patent Application No. 20060263423 to SPI Pharma, Inc. discloses a method for preparing highly compactible carbohydrate comprising blending a first carbohydrate and a second carbohydrate, the first carbohydrate has a melting point higher than the second carbohydrate; melting the second carbohydrate over the first carbohydrate to obtain a highly compacted product, drying the product, and screening the product to desired particle size. The reference discloses that erythritol may be used as one of the carbohydrates.

U.S. Published Patent Application No. 20070026121 to Benedict et al. discloses a sweetening composition having a crystalline matrix that contains a first material and a second material. The reference discloses that the first material may be erythritol and that the second material may be sucralose.

U.S. Published Patent Application No. 20100222311 to Purdue Research Foundation discloses pharmaceutical compositions that contain a solid suspension comprising an active pharmaceutical ingredient and a pharmaceutically acceptable water soluble solid additive, wherein at least a portion of the active pharmaceutical ingredient and a portion of the pharmaceutically acceptable water soluble solid additive are present as crystals in the solid suspension. The reference discloses that erythritol and malic acid are suitable water soluble solid additives.

U.S. Pat. No. 4,886,677 to Mistubishi Kasei Corporation discloses a surface modified meso-erythritol composition, wherein the surface of meso-erythritol is modified with water, non-saccharide sweetening agents, sugar alcohols and/or saccharides. The composition is obtained by mixing meso-erythritol crystal grains and meso-erythritol powders, adding water to the resulting mixture, kneading the mixture, compression-molding the mixture, and drying the resulting molded product.

U.S. Pat. No. 5,080,916 to Mitsubishi Kasei Corporation and Nikken Chemicals Company Limited discloses a sweetening composition that contains microcrystalline meso-erythritol particles whose surface is coated with a sweetening component. The composition is prepared by kneading erythritol with a sweetening component to coat the erythritol.

U.S. Pat. No. 6,030,820 to Mitsubishi Chemical Company discloses a process for producing a high-purity erythritol crystal.

U.S. Pat. Nos. 6,475,552 and 6,559,302 to Shah et al. disclose an edible polysaccharide prepared by reacting a polyol with a saccharide in the presence of mineral acid under anhydrous melt polymerization conditions. The references disclose that the polyol may be erythritol, that the saccharide may be glucose, other simple sugars, hydrolyzed starch and mixtures thereof and that the acid may be malic acid.

U.S. Pat. No. 6,875,460 to SPI Polyols, Inc. discloses a co-crystallized polyol and hydrogenated maltodextrin sweetener. The reference discloses co-melting a polyol, e.g., erythritol, with hydrogenated maltodextrin to form a fully melted mixture. The reference discloses that the resulting mixture has a reduced cooling effect compared to the original polyol.

U.S. Pat. Nos. 8,277,862 and 8,277,862 to Concentrate Manufacturing Company of Ireland disclose beverage products that contain rebaudioside A, erythritol and an acid component. The references disclose that malic acid is an exemplary acid component.

Co-pending U.S. Patent Publication No. 20090104326 to Catani et al. discloses a solid sweetening composition having erythritol and a secondary sweetener in a single solid matrix. The reference discloses that the solid sweetening composition may be made by: a) heating the erythritol, wherein only enough heat is provided to melt a portion of the erythritol; b) mixing the secondary sweetener into the partially melted erythritol to obtain a mixture; c) cooling the mixture until the mixture is solid; and d) grinding the solid mixture to desired particle size, wherein the erythritol is at least about 50% by weight of the solid sweetening composition. Turbinado sugar is the secondary sweetener used in the examples.

Co-pending U.S. Patent Publication No. 20090011104 discloses a solid sweetening composition having erythritol and a complex sweetener in a single matrix, wherein the composition is produced by melting erythritol, adding the complex sweetener to the melted erythritol, cooling the mixture and grinding the resulting mass.

Co-pending U.S. Published Application No. 2009004355 discloses the use of *stevia* extracts, including rebaudioside-A, to remove brightness from the taste of erythritol.

What is needed is a sweetening composition that is stable and produces a favorable flavor profile for use in consumer products. The method of the invention provides the ability to achieve controlled particle size, uniform blend using a range of commercial actives, improved yield, improved quality, enhanced stability and cost savings.

SUMMARY OF THE INVENTION

The present invention is directed to a partial melt co-crystallization composition comprising, consisting of and/or consisting essentially of a crystallizable carrier and an active.

The present invention is further directed to a method for producing a co-crystallization composition comprising, consisting of and/or consisting essentially of a crystallizable carrier and an active, wherein the method comprises, consists of and/or consists essentially of:

partially melting the crystallizable carrier in an aqueous solution;

mixing the active into the partially melted crystallizable carrier to obtain a mixture; and applying a vacuum to remove water; and allowing the mixture to re-crystallize.

Crystals having uniform size with active co-crystallized in a matrix are thus formed.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE DRAWINGS

The accompanying drawings, which are incorporated in and constitute a part of this specification, illustrate embodiments of the invention, and together with the description, explain the principles of the invention. In the drawings.

DETAILED DESCRIPTION OF THE INVENTION

As used herein, the term "active" means a substance in a consumer product that is biologically active.

As used herein, the term "crystallizable carrier" means a substance that is able to form solid crystals and that facilitates the transport of an active. Preferred crystallizable carriers are sugars and sugar alcohols. A more preferred crystallizable carrier is erythritol. Additional carriers include isomalt and salt.

As used herein, a "food-grade" material is one that conforms to the standards for foods deemed safe for human consumption set forth in the Codex Alimentarius produced by the World Health Organization (1999).

As used herein, the term "high intensity sweetener" or "HIS" means a substance that provides a high sweetness per unit mass compared to a nutritive sweetener and provides little or no nutritive value. Many high intensity sweeteners are known to those skilled in the art and any may be used in the present invention. Examples of high intensity sweeteners include, for example, aspartame, acesulfame, alitame, brazien, cyclamic acid, dihydrochalcones, extract of *Dioscorophyllum cumminsii*, extract of the fruit of *Pentadiplandra brazzeana*, glycyrrhizin, hernandulcin, mogroside, monellin, neotame, neohesperidin, saccharin, sucralose, any of the glycosides of the aglycone steviol including, but not limited to stevioside, rebaudioside A, rebaudioside B, rebaudioside C, rebaudioside D, rebaudisode E, rebaudisode F, dulcoside, rubusoside, steviolmonoside, steviolbioside, and 19-O-β glucopyranosol-steviol, thaumatin, extracts of sweet plants, such as *stevia* and luo han gou, and combinations thereof. A preferred high intensity sweetener according to the present invention is luo han guo. Another preferred high intensity sweetener according to the present invention is *stevia*.

As used herein the term "partially melted erythritol" (or "partially melted crystallizable carrier") means a composition, with or without other ingredients or components that has been heated to a temperature sufficient to melt part of the erythritol (or crystallizable carrier) to provide a slurry of melted and solid erythritol (or crystallizable carrier). A preferred range for melting is about 5% to about 60% by weight of the erythritol (or crystallizable carrier). A preferred range for melting for a low active load is about 10% to about 30% by weight of the erythritol (or crystallizable carrier). A preferred range for melting for a high active load is about 20 to about 40% by weight of the erythritol (or crystallizable carrier).

As used herein, the term "pharmaceutical active" means the substance in a pharmaceutical drug that is biologically active.

The pharmaceutical active may be a pharmaceutical active for immediate or sustained release. Such pharmaceutical active may be formulated for immediate release upon ingestion, for sustained release, for release in the colon, or any combination thereof.

The pharmaceutical active may be an antihistamine, a decongestant, an analgesic, an anti-inflammatory, an antipyretic, a cough suppressant, an expectorant, or any other pharmaceutical active or combination of such pharmaceutical actives.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof, and pharmaceutically acceptable salts and esters thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof, and pharmaceutically acceptable salts and prodrugs thereof.

Examples of cough suppressants and expectorants include, but are not limited to, diphenhydramine, dextromethorphan, noscapine, clophedianol, menthol, benzonatate, ethylmorphine, codeine, acetylcysteine, carbocisteine, ambroxol, belladona alkaloids, sobrenol, guaiacol, and guaifenesin; isomers thereof, and pharmaceutically acceptable salts and prodrugs thereof.

Additional examples of actives include eucalyptol, menthol, methyl salicyate and thymol.

Preferred actives include heat sensitive and/or moisture sensitive actives.

As used herein, a gram (or other given amount) of Sucrose Equivalent Sweetness ("SES") means the amount of high intensity sweetener needed to be added to an 8 ounce glass of water in order to provide the same sweetness as an independent 8 ounce glass of water containing one gram (or the other given amount) of sucrose. For example, 1/200 g of aspartame will equal about one gram of SES because aspartame is about 200 times sweeter than sucrose. Similarly, about 1/500 g to about 1/600 g of sucralose will provide one gram of SES because sucralose is about 500 to about 600 times sweeter than sucrose. Monk fruit is 4× as sweet as sucrose and is thus equal to about 0.25 gram SES per gram sucrose.

As used herein, the term "sugar alcohol" means a food-grade alcohol derived from a sugar molecule. Sugar alcohols useful in the present invention include, for example, dextrose, fructose, isomalt, erythritol, hydrogenated isomaltulose, hydrogenated starch hydrolyzates, lactitol, maltitol, mannitol, polydextrose, sorbitol, sucrose, tagatose, trehalose, xylitol, and combinations thereof.

As used herein the term "sweetening active" means a food additive that duplicates the effect of sugar taste. A preferred sweetening active is a high intensity sweetener.

As used herein, all numerical ranges provided are intended to expressly include at least all numbers that fall between the endpoints of ranges.

The preferred ratio of crystallizable carrier to active is at least about 5% to about 40% by weight for foods, about 0.5% to about 20% by weight for sweeteners and about 5% to about 50% by weight for prescription and/or over-the-counter drugs.

The active can be a sweetening active or a pharmaceutical active. The compositions contemplated herein can be a mixture of several actives and crystallizable carriers. The composition can contain other sweeteners, sugars, fibers or nutritional components that are stable under partial melt conditions. The compositions of the present invention may contain additional non-sweetening ingredients as well, including flavors, aromas, other nutritional components, and mixtures thereof. For example the compositions can contain fiber(s), vitamin(s), mineral(s), and/or herbal supplement(s).

The compositions of the present invention have SES's that are higher than erythritol, preferably greater than about 0.25 grams SES per gram.

As used herein, unless otherwise indicated, the term "flavor" means any food-grade material that may be added to the present compositions to provide a desired flavor. Flavors useful in the present invention include, for example, cream, hazelnut, vanilla, chocolate, cinnamon, pecan, lemon, lime, raspberry, peach, mango, vanillin, butter, butterscotch, tea, orange, tangerine, caramel, strawberry, banana, grape, plum, cherry, blueberry, pineapple, elderberry, watermelon, bubblegum, cantaloupe, guava, kiwi, papaya, coconut, mint, spearmint, derivatives, and combinations thereof.

As used herein, unless otherwise indicated, the term "aroma component" means any food-grade volatile substance that may be employed to produce a desired scent, for example, when mixed with a foodstuff Aromas useful in the present invention include, for example, essential oils (citrus oil), expressed oils (orange oil), distilled oils (rose oil), extracts (fruits), anethole (liquorice, anise seed, ouzo, fennel), anisole (anise seed), benzaldehyde (marzipan, almond), benzyl alcohol (marzipan, almond), camphor (*cinnamomum camphora*), cinnamaldehyde (cinnamon), citral (citronella oil, lemon oil), d-limonene (orange) ethyl butanoate (pineapple), eugenol (clove oil), furaneol (strawberry), furfural (caramel), linalool (coriander, rose wood), menthol (peppermint), methyl butanoate (apple, pineapple), methyl salicylate (oil of wintergreen), neral (orange flowers), nerolin (orange flowers), pentyl butanoate (pear, apricot), pentyl pentanoate (apple, pineapple), sotolon (maple syrup, curry, fennugreek), strawberry ketone (strawberry), substituted pyrazines, e.g., 2-ethoxy-3-isopropylpyrazine; 2-methoxy-3-sec-butylpyrazine; and 2-methoxy-3-methylpyrazine (toasted seeds of fenugreek, cumin, and coriander), thujone (juniper, common sage, Nootka cypress, and wormwood), thymol (camphor-like), trimethylamine (fish), vanillin (vanilla), and combinations thereof. Preferred aroma components according to the present invention include, essential oils (citrus oil), expressed oils (orange oil), distilled oils (rose oil), extracts (fruits), benzaldehyde, d-limonene, furfural, menthol, methyl butanoate, pentyl butanoate, salts, derivatives, and combinations thereof.

The aroma component may be present in any amount in the composition. Preferably, the aroma component is present in an amount from about 2- to about 10-times the detectable amount. More preferably, the aroma component is present in an amount from about 2- to about 5-times the detectable amount. As used herein, unless otherwise indicated, the term "detectable amount" is the amount of the aroma component required to produce a scent detectable in the foodstuff.

The compositions of the present invention have energy contents less than that of a nutritive sugar, preferably less than 5 calories per serving.

Unlike dry blends of the ingredients used in the inventive composition, the partial melt co-crystallization compositions of the present invention are a crystalline matrix. This form assures consistent delivery and taste in a system and prevents parts of the composition from having distinctly different tastes. Pharmaceutical benefits include improved active stability (heat stability); assured active uniformity; and reduced active waste and/or improved active yield.

As a sweetener, the composition can be packaged in packets, as a bulk sweetener, in cubes, or any normal sugar forms.

As a pharmaceutical, the composition can be any solid object, semi-solid, or liquid-filled composition designed to contain a specific pre-determined amount (dose) of a pharmaceutical active.

Compositions of the present invention may be made by any methods known to those skilled in the art. These methods produce a solid, stable, no-sticky, homogeneous, composition from a crystallizable carrier and an active. All of the methods involve:

Partially melting a crystallizable carrier in an aqueous solution;

mixing in an active; and applying a vacuum to the mixture to evaporate the water.

Alternatively the order can be adjusted as follows: combining the crystallizable carrier and active to form a mixture; partially melting the crystallizable carrier in the mixture; and drying the mixture.

The amount of crystallizable carrier and of active can be any amount that provides for the desired taste profile and calorie content. Preferably, the crystallizable carrier makes up over about 60% to about 80% by weight of the composition.

An important aspect of the invention is the control of the degree of melting of the crystallizable carrier. By providing only enough heat to melt a portion of the crystallizable carrier used in the composition, a much more homogeneous matrix can be made. This embodiment of the present invention not only provides a more homogeneous matrix but also saves energy, and simplifies process and quality controls.

The degree of liquefying/melting is calculated from the quantity of water added. The quantity of water is multiplied with the solubility of erythritol in water. The preferred range of liquefying/melting is about 25%.

For hot melt, one way to determine degree of melting is set forth below:

Assume the batch weight is 100 g. If one hot melts (complete liquefying) 30 grams, and then add active to the liquefied melt for uniform mix and then adds the remaining 70 grams, the degree of melt would be 30% (30 grams melt over 100 grams total weight). This example will be applicable for sugar based co-crystallization which uses small amounts of water to reduce melting point and combine with heat to melt the 30% sugar so actives can be mixed in uniformly.

The degree of melting can be any amount that provides for a homogeneous suspension. The degree of melting of the crystallizable carrier can be between about 10% and about 40% of the matrix. Most preferable, the degree of melting is the maximum amount of melting that maintains a slurry.

The melting can be done in a confectioner's pan, a kettle, an agitated vessel, a heated screw feeder or extruder, crystallizer or the like. It can be continuous, batch or semi-batch. Heat can be provided by any means know to those skilled in the art. Drying can be done batch-wise or continuously, or a combination. It can be done in pans, on a cooling wheel or belt, or any other means known to those skilled in the art.

The method of the invention permits independent control over flavor and sweetness levels. One especially useful aspect of the invention is that the homogeneous nature of the resultant compositions ensure even and stable distribution of the sweetening active, and prevent separation, which minimizes highly sweet areas common with simple dry blend compositions. Pharmaceutical benefits include uniform active distribution; protect heat labile pharmaceutical actives, especially when vacuum is applied; and minimizes medicinal or bitter notes of pharmaceutical actives.

While erythritol is described herein, any crystallizable carrier can be used in place of erythritol in the present invention. Additionally, any active, regardless of its melting point or miscibility within the crystallizable carrier can be used.

One aspect of the processes included in the present invention is that the temperature to provide the homogeneous matrix does not need to reach the melting point of the active. This permits lower processing temperatures than would otherwise be needed. Using such temperature can minimize and potentially eliminate the development of undesirable flavor notes.

Minimizing the amount of heat needed is an important aspect of the invention. To this end it is useful that the actives do not actually melt in the processing of the solid matrix. While this has been desirable in the past to assure homogeneity of the final solid matrix it will be now clear to those skilled in the art that using the methods disclosed herein, it is no longer necessary. This not only saves energy, but it speeds up processing time.

The following examples are provided to further illustrate the compositions and methods of the present invention. These examples are illustrative only and are not intended to limit the scope of the invention in any way.

EXAMPLES

Edible crystals with melting temperatures below 200° C. can effectively be partially melted and co-crystallized with active ingredients such as natural or artificial sweeteners or nutrients and then co-crystallized with good sheen. Edible crystals with melting temperatures higher than 200° C. can either be partially melted or can be prepared in aqueous solutions and added to a partially melted crystal at lower temperature and co-crystallized. Partial melt requires less energy than full melt and results in improved crystal appearance and sheen. Due to less heat exposure, partial melt delivers clean sensory quality. For example, natural sweeteners such as *Stevia*, Reb A, D, luo han guo extract and luo han guo juice can easily be co-crystallized with erythritol as well as with artificial sweeteners. Partial melt enhances process stability by reducing and/or eliminating thermal degradation and reactive species produced. The resulting crystals are more stable, have a better taste profile and one of improved quality, while looking, tasting and sounding like sugar.

Erythritol was partially melted at 85-90° C. in a heated vessel or crystallizer. Sweeteners or nutrients solutions were then added, mixed and slowly co-crystallized by reducing batch temperature to around 50-60° C. over a 3-4 hour period. The resulting co-crystallized product has crystal sheen and good taste quality. Heat sensitive actives/ingredients and their stability are also improved as limited heat is applied during the partial melt operation.

In accordance with the invention, a composition comprising an edible crystallizable carrier containing either sweetening actives or pharmaceutical actives is prepared by:

melting a crystallizable carrier in an aqueous solution;

mixing in an active; and applying vacuum to evaporate water.

The resulting co-crystallized sweetener composition improves sweetness sensation with controllable crystal size and appearance. Similarly, the resulting pharmaceutical co-crystallized actives are more stable and uniform with much more reduced bitter or medicinal notes.

Additionally, the benefits of this partial melting and co-crystallization process include higher product yield, improved product stability and active content uniformity.

To offer sugar-like crystalline sugar substitutes with good sheen and desirable size distribution, so that the co-crystallized product looks, feels, and sounds like sugar.

To offer crystallized pharmaceutical products with much less bitter or medicinal notes plus offering product stability.

Other approaches have focused on coating, agglomeration or spray drying processes, which do not retain crystal grains with sheen. Meanwhile, coating does not improve content uniformity and/or reduce bitterness/off notes.

Firstly, currently partial melt technology using aqueous solution to melt the surface of crystals and then re-crystallize by using vacuum to evaporate the water. Thus, minimal heat was involved which preserve heat sensitive actives.

Secondarily, the current product demonstrates that such co-crystallized product minimize bitter and medicinal notes significantly in applications.

Introducing sweetening active or pharmaceutical active during carrier crystallization process to immerse and co-crystallize so that the resulting crystals have actives included thereon.

Allow the co-crystallized crystals to dry overnight at room temperature

The following example demonstrates the benefits of partial melt co-crystallization technology (CCT) in reducing sour notes (via malic acid, a food acid that can be safely consumed). The data show unique benefits including homogeneity of active, uniformity and ease of control of particle size, as well as shorter process time and high product yield.

Below are the co-crystallized erythritol/malic acid sensory results, which are in the form of a triangle test with reasons for choosing the odd sample.

Figure 2:
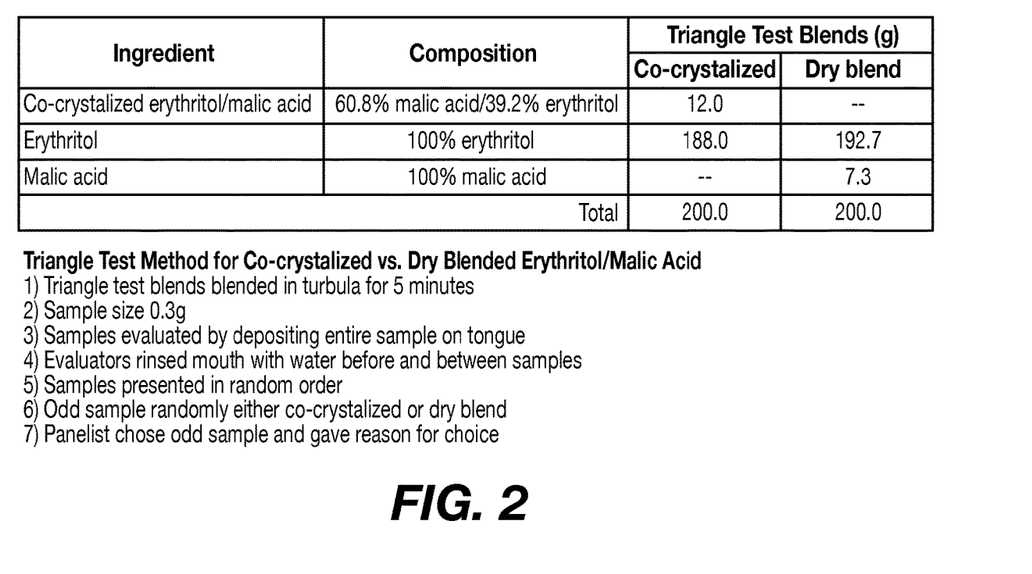
FIG. 2 is a table showing the methodology employed in the co-crystallized v. dry blend erythritol/malic acid triangle test.
Figure 3:
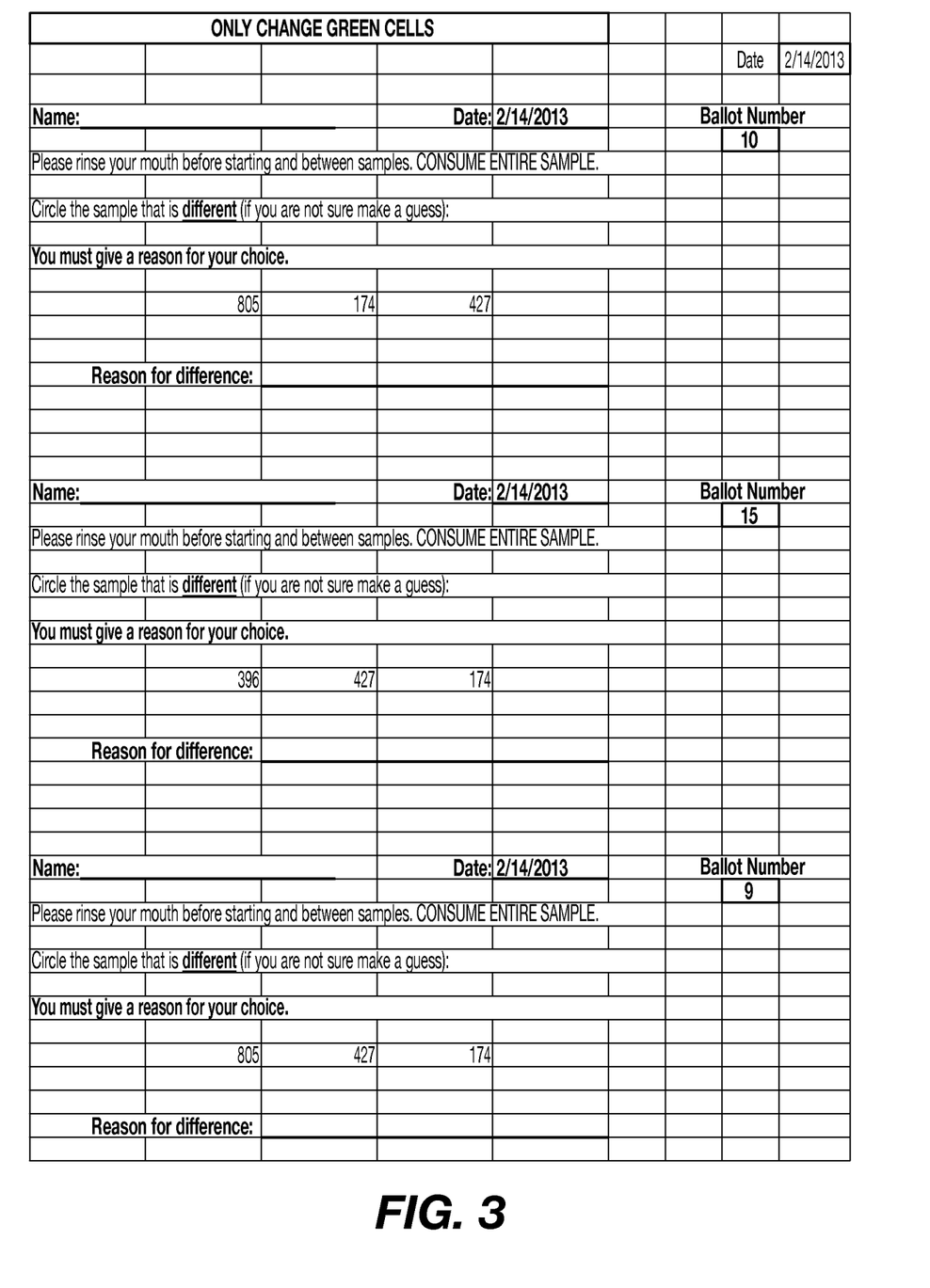
FIG. 3 is a sample questionnaire for the co-crystallized v. dry blend erythritol/malic acid triangle test.
Figure 4:
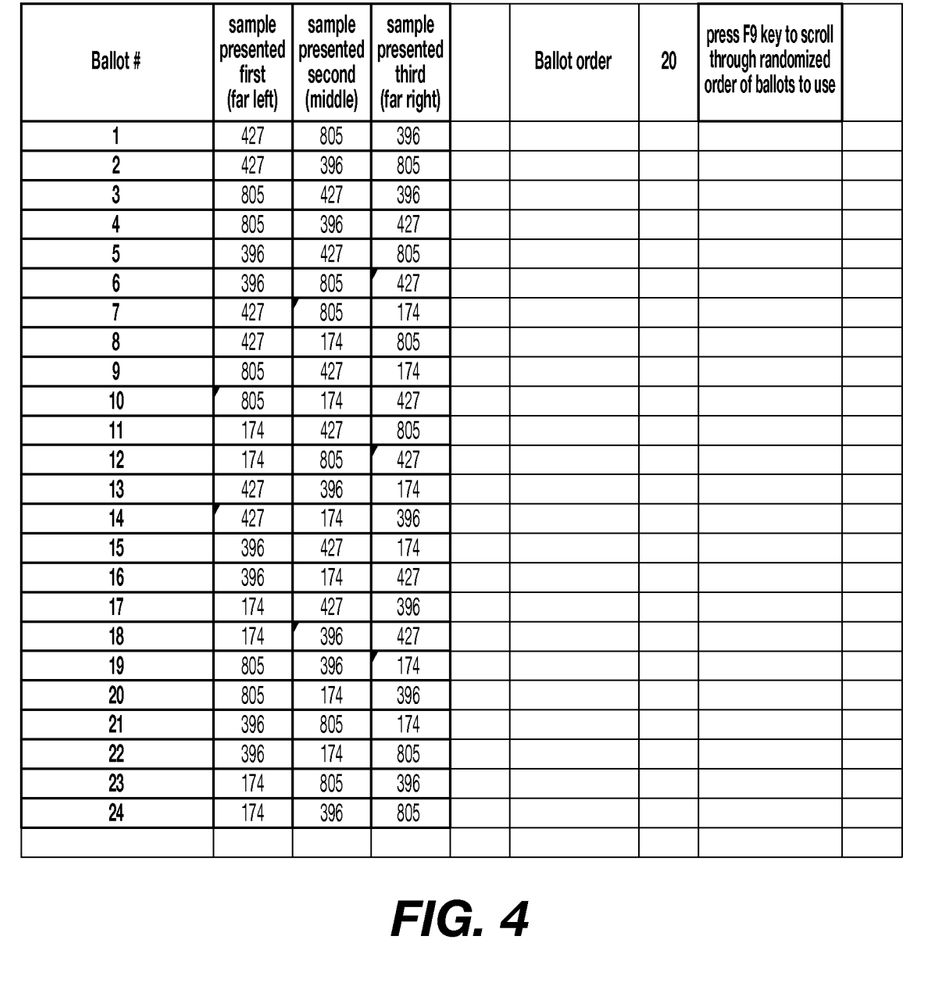
FIG. 4 is a table showing the methodology used to randomize the co-crystallized v. dry blend erythritol/malic acid triangle test.

The triangle test was conducted to determine whether a sensory difference existed between the co-crystallized products of the invention. It is useful in situations where treatment effects might have produced product attribute changes. The test is conducted by presenting to each panelist three coded samples, in which two samples are identical and the other is different (or odd) sample. Panelists are asked to taste each sample from left to right and select the odd sample. The number of correct replies are counted and analyzed. The methodology is set forth in FIG. 2; a sample questionnaire is shown in FIG. 3; and the methodology to randomize is set forth in FIG. 4.

Since the % malic acid in the co-crystallized material was very high, the panel received a blend of co-crystallized material and erythritol. The dry blend only was formulated to match the over % malic acid in the co-crystallized blend (total malic acid for both triangle test blends 3.65%).

| | Erythritol Malic acid | Erythritol PureFruit ™ Select(*) Molasses | Erythritol Luo han go | Erythritol Luo han go Molasses | Erythritol Stevia | Erythritol Stevia Molasses |
|---|---|---|---|---|---|---|
| Co-crystallized blend | | | | | | |
| Dry blend | | | | | | |

(*)PureFruit by Tate & Lyle is extract from monk fruit.
Examples on co-crystallization technology.

Partial-melt of crystals can be achieved by using heat at temperatures about 5-10° below a crystal's melting temperature (or if vacuum is applied, the melting temperature can be significantly reduced to protect heat sensitive actives) so that crystals will be partially melted at the surface. Depending on the quantity of active to be co-crystallized, a target of 10-40% melting can be devised. For water soluble crystals, partial melt can be achieved by using aqueous solution to melt the surface before co-crystallization with actives. With aqueous solution, minimum heat is needed, this is important for heat liable ingredients.

Example 1

Erythritol Co-Crystallized with Malic Acid

Co-crystallization compositions were made as follows:
Heat 100 mL water to about 70° C. in beaker
Start stirring and add 160 g erythritol, until completely dissolved
Add 240 g malic acid and keep stirring until completely dissolved
Allow to cool down slowly
When reach about 25° C., vacuum filter the mixture
Collect and weigh the filtrate The molasses in the final product (69.4% CCB: ERY+PureFruit™ Select+molasses, 30.6% EFG sugar) is aimed at 0.8%.

Results

Figure 1A:
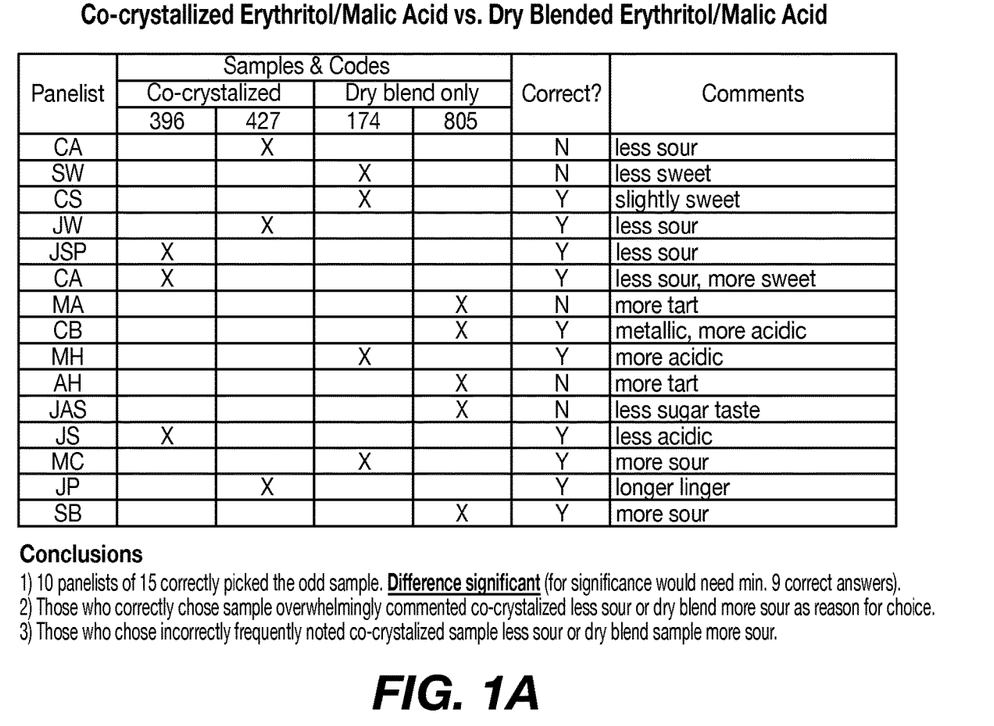
FIG. 1A and FIG. 1B are a table and a graph, respectively, showing the co-crystallized v. dry blend erythritol/malic acid triangle test sensory results.
Figure 1B:
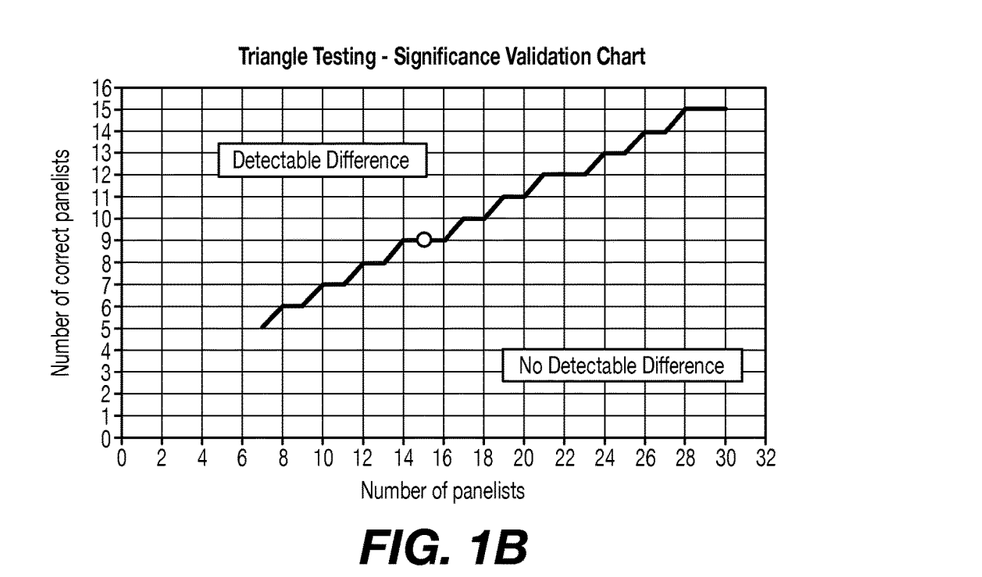

Results are shown in FIGS. 1A and 1B. FIG. 1A shows the raw data results and FIG. 1B graphically represents the results. For the triangle test, 10 out of 15 panelists correctly chose the odd sample, making it a significant difference (≥9). The difference noted by panelists was overwhelmingly "less sour" for the co-crystallized blend and "more sour" for the dry blend.

Example 2

The current process mainly using aqueous (water) solution to partially melt the crystals, thus minimum heat is applied which is important for heat liable actives. It is a process that can easily be controlled with fast process time. With less heat, good product quality can always be assured. Particle size distribution can be controlled via this partial melt co-crystallization.

Partial-Melt Co-Crystallization for Controlled Crystal Size Distribution

Size data was obtained on erythritol co-crystallized with monk

| Mesh size | Batch I, % Before* | Batch I, % After** | Batch II, % Before | Batch II, % After | Batch III, % Before | Batch III, % After | Batch IV, % Before | Batch IV, % After |
|---|---|---|---|---|---|---|---|---|
| >20 | 0 | 0 | 0 | 0.4 | 0 | 0.6 | 0 | 0 |
| 20-30 | 1.1 | 8.8 | 30.5 | 30.8 | 30.5 | 29.4 | 30.5 | 22.9 |
| 30-40 | 85 | 68.5 | 45.6 | 47.1 | 45.6 | 48.5 | 45.6 | 51.0 |
| 40-50 | 13.7 | 21 | 22.1 | 19.8 | 22.1 | 19.0 | 22.1 | 24.2 |
| 50-60 | 0 | 1.1 | 0.6 | 1.2 | 0.6 | 1.9 | 0.6 | 1.3 |
| <60 | 0 | 0.6 | 1.3 | 0.4 | 1.1 | 0.5 | 1.1 | 0.5 |
| Product yield | 95% | | 97% | | 97% | | 99% | |

*Before: before partial-melt co-crystallization
**After: after partial-melt co-crystallization The numbers in the table above are consistent from batch to batch, if same degree of melt is maintained (controlled by quantity of water added and heat). Size numbers can be manipulated by degree of melt. For example, when more water is added (more melt), the additional water will dissolve more of the small crystals, thus when re-crystallizing, the resulting crystals size will tend to be bigger (i.e., more melt get bigger size).

Example 3

Luo Han Guo Extract with Erythritol

Erythritol-PureFruit™ Select
A water bath is set at temperature 83° C. 400 grams of erythritol is weighed and put in the water bath. 15 grams of PureFruit™ Select (50% mogroside V and 50% carbohydrates and proteins) and 22.5 grams of water are mixed together at 60° C. to make 40% solid solution. Then 25 grams of solution with PureFruit™ Select is gradually added to dissolve erythritol crystals while stirring. The solution is able to dissolve/melt approximately 20%-35% crystal's outer surface. The melted/dissolved crystals were slowly dried which allows crystals to re-crystallized into new crystal grains with sheen. The resulting crystals have actives entrapped from the inside to the surface of the re-crystallized grains.

Example 4

Luo Han Guo Extract, Molasses with Erythritol

Erythritol-PureFruit™ Select-Molasses
A water bath is set at temperature 83° C. 400 grams of erythritol is weighed and put in the water bath. 15 grams of PureFruit™ Select and 22.5 grams of water are mixed together to make 40% solid solution. Then 8 grams of molasses is added to 40% solid solution. 25 grams of solid solution is gradually added to erythritol to melt crystal grains while stirring. The melted/dissolved crystals were slowly dried which allows crystals to re-crystallized into new crystal grains with sheen. The resulting crystals have actives entrapped entrapped from the inside to the surface of the re-crystallized grains.

Example 5

Stevia Extract with Erythritol

Erythritol-Stevia
A water bath is set at temperature 83° C. 100 grams of erythritol is weighed and put in the water bath. 4.5 grams of Tasteva™ (98% Reb A) and 10.5 grams of water are mixed together to make 30% solid solution. Then 10 grams of solid solution is gradually added to erythritol while stirring. The melted/dissolved crystals were slowly dried which allows crystals to re-crystallized into new crystal grains with sheen. The resulting crystals have actives entrapped entrapped from the inside to the surface of the re-crystallized grains.

Example 6

Stevia Extract, Molasses with Erythritol

Erythritol-Stevia-Molasses
A water bath is set at temperature 83° C. 200 grams of erythritol is weighed and put in the water bath. 9 grams of Tasteva™, 21 grams of water are mixed together to make 30% solid solution. Then 2.16 grams of molasses is added to 30% solid solution. 22 grams of solid solution is gradually added to erythritol to melt crystal grains while stirring. The melted/dissolved crystals were slowly dried which allows crystals to re-crystallized into new crystal grains with sheen. The resulting crystals have actives entrapped from the inside to the surface of the re-crystallized grains.

Example 7

Samples were prepared in accordance with the method below.
A water bath is set to 80° C.
400 grams of erythritol is put in a beaker in the water bath
15 grams of PureFruit™ Select and 22.5 grams of water are mixed together to make a 40% solid solution
Then 8 gram of molasses is added to the 40% solid solution Then 25 grams of the monk solution is slowly added to the erythritol while stirring The added the aqueous solution will dissolve about 25% of erythritol Continued slowly mixing the mixture in 80° C. water batch to allow the mixture to re-crystallize until a dry power is obtained.

TABLE 2

Density of Co-Crystallized Samples

| Samples | Density (g/cc) |
| --- | --- |
| Erythritol-Stevia I | 0.786 |
| Erythritol-Stevia with Reb D | 0.796 |
| Erythritol-Stevia and Reb D | 0.770 |
| Erythritol-Stevia I-molasses | 0.778 |
| Erythritol-Stevia I & Reb D-molasses | 0.780 |
| Erythritol-Stevia I and Reb D-molasses | 0.788 |

Example 8

Sugar with Reb D co-crystals were prepared in accordance with (1) and (2) below.

Example 8(1)

a) Set water bath temperature at 83° C.
b) Weigh 60 g of sugar into 1 L beaker, add 8 g of water, and microwave for 15 s to melt.
c) Mix in active (7 g of Reb D) then add the remaining sugar (140 g).
d) Put the beaker into water bath, keep stirring until obtain dry powder.

Example 8(2)

a) Set water bath temperature at 83° C.
b) Weigh 7 g of Reb D and 10 g of water into 1 L beaker to make a suspension.
c) Add 200 g of sugar.
d) Put the beaker into water bath, keep stirring until obtain dry powder.

Sugar with RightSweet™ co-crystals were prepared in accordance with (3) and (4) below. RightSweet™ in this instance regards RightSweet stevia, which contains Reb A (90%) and Reb D (7%).

Example 8(3)

The procedure is same to Example 8(1) except for using 6 gram of RightSweet™.

Example 8(4)

The procedure is same to Example 8(2) except for using 6 gram of RightSweet™ and 6 gram of water.

Erythritol, Sugar with PureFruit™ Select co-crystals were prepared in accordance with (5) below

Example 8(5)

a) Set water bath temperature at 83° C.
b) Prepare actives in a 60% solid solution: dissolve 12.7 grams of PureFruit™ Select and 4.38 grams of molasses into 11.38 grams of water.
c) Weigh 140 grams of erythritol and 60 grams of sugar into 1 L beaker and put it into water bath.
d) Gradually add 12.7 grams of solid solution to dissolve erythritol/sugar while stirring until obtain dry powder.

Erythritol with PureFruit™ Select co-crystals were prepared in accordance with (6) below.

Example 8(6)

a) Set water bath temperature at 83° C.
b) Make 40% solid solution: dissolve 12.7 grams of PureFruit™ Select into 19.05 grams of water.
c) Weigh 200 grams of erythritol into 1 L beaker and put it into water bath.
d) Gradually add 12.7 grams of solid solution to dissolve erythritol while stirring until obtain dry powder.

Isomalt with RightSweet™ co-crystals were prepared in accordance with (7) below.

Example 8(7)

a) Set water bath temperature at 83° C.
b) Weigh 6 g of Isomalt and 6 g of water into 1 L beaker to make a suspension.
c) Add 200 g of Isomalt.
d) Put beaker into water bath, keep stirring until obtain dry powder.

Example 9

Preparation of Listerine® Powdered Mouthwash Using Partial Melt Co-Crystallization Technology

Example 9(a)

Same Active Ingredients as Listerine® Original

The active ingredients listed on Listerine® bottles are essential oils which are menthol, thymol, methyl salicylate and eucalyptol.

Procedure:

Put a water bath in a fume hood, and set temperature at 83° C. Weighed 100 g of erythritol into a 1 L beaker and put it in the water bath. In a 100 mL beaker, added 0.84 g of menthol and 1.28 g of thymol into 8 g of water. Weighed 1.2 g of methyl salicylate and 1.84 g of eucalyptol and put into the same 100 mL beaker to make a suspension. Then added the suspension slowly into the 1 L beaker containing partially melted erythritol. In this process, all other actives were evenly dispersed in the erythritol solute. The solute was then re-crystallized, and the actives were uniformly enclosed in the co-crystals. Kept stirring until obtained dry powders. This unique process significantly reduced process cost, and enhanced product quality and stability.

Use direction: dissolve 1 g of powder into 20 mL water and rinse for 30 seconds.

Example 9(b)

Same Active Ingredients as Listerine® (Add Sucralose)

Procedure:

Put a water bath in a fume hood, and set temperature at 83° C. Weighed 100 g of erythritol into a 1 L beaker and put it in the water bath. In a 100 mL beaker, added 0.84 g of menthol and 1.28 g of thymol into 8 g of water. Weighed 1.2 g of methyl salicylate, 1.84 g of eucalyptol and 0.6 g of sucralose into the same 100 mL beaker to make a suspension. Then added the suspension slowly into the 1 L beaker containing the partially melted erythritol. In this process, all other actives were evenly dispersed in the erythritol solute. The solute was then re-crystallized, and actives were uniformly enclosed in the co-crystals. Kept stirring until obtained dry powders. This unique process significantly reduced process cost, and enhanced product quality and stability.

Use direction: dissolve 1 g of powder into 20 mL water and rinse for 30 seconds.

Example 9(c)

Same Active Ingredients as Listerine® (Xylitol Replace Erythritol)

Procedure:

Put a water bath in a fume hood, and set temperature at 83° C. Weighed 100 g of xylitol into a 1 L beaker and put it in the water bath. In a 100 mL beaker, added 0.84 g of menthol and 1.28 g of thymol into 5 g of water. Weighed 1.2 g of methyl salicylate, 1.84 g of eucalyptol and 0.6 g of sucralose into the same 100 mL beaker to make a suspension. Then added the suspension slowly into the 1 L beaker to partially melted xylitol. In this process, all other actives were evenly dispersed in the xylitol solute. The solute was then re-crystallized, and actives were uniformly enclosed in the co-crystals. Kept stirring until obtained dry powders. This unique process significantly reduced process cost, and enhanced product quality and stability.

Use direction: dissolve 1 g of powder into 20 mL water and rinse for 30 seconds.

Example 9(d)

Same Active Ingredients as Listerine® (Add Mint Flavor)

Procedure:

Put a water bath in a fume hood, and set temperature at 83° C. Weighed 100 g of xylitol into a 1 L beaker and put it in the water bath. In a 100 mL beaker, added 0.84 g of menthol and 1.28 g of thymol into 5 g of water. Weighed 1.2 g of methyl salicylate, 1.84 g of eucalyptol, 0.6 g of sucralose and 0.83 g of mint flavor into the same 100 mL beaker to make a suspension. Then added the suspension slowly into the 1 L beaker to partial melt xylitol. In this process, all other actives were evenly dispersed in the xylitol solute. The solute was then re-crystallized, and actives were uniformly enclosed in the co-crystals. Kept stirring until obtain dry powders. This unique process significantly reduced process cost, and enhanced product quality and stability.

Use direction: dissolve 1 g of powder into 20 mL water and rinse for 30 seconds.

Example 9(e)

Same Active Ingredients as Listerine® (Add Alcohol Replacer)

Procedure:

Put a water bath in a fume hood, and set temperature at 83° C. Weighed 100 g of xylitol into a 1 L beaker and put it in the water bath. In a 100 mL beaker, added 0.84 g of menthol and 1.28 g of thymol into 5 g of water. Weighed 1.2 g of methyl salicylate, 1.84 g of eucalyptol, 0.6 g of sucralose, 0.83 g of mint flavor and 1.65 g of alcohol replacer into the same 100 mL beaker to make a suspension. Then added the suspension slowly into the 1 L beaker to partial melt xylitol. In this process, all other actives were evenly dispersed in the xylitol solute. The solute was then re-crystallized, and actives were uniformly enclosed in the co-crystals. Kept stirring until obtain dry powders. This unique process significantly reduced process cost, and enhanced product quality and stability.

Use direction: dissolve 1 g of powder into 20 mL water and rinse for 30 seconds.

The foregoing examples are not intended to limit the scope of the present invention, which may be set out in the claims. In particular, various equivalents and substitutions will be recognized by those skilled in the art in view of the foregoing disclosure and these are contemplated to be within the scope of the invention.

The invention claimed is:

1. A method of making a co-crystallization composition consisting of: co-crystallizing malic acid and an initial amount of erythritol using a weight ratio of 3:2 malic acid to the initial amount of erythritol; and wherein the co-crystallized material is blended with additional erythritol.

2. The method of claim 1 wherein the malic acid is completely dissolved in water at a temperature of about 70° C.; the initial amount of erythritol is then completely dissolved the water; and the solution is allowed to cool to about 25° C.

3. The method of claim 1 wherein the total malic acid amount in the final mixture is 3.65% by weight compared to the total weight of co-crystalized material and additional erythritol.

4. The method of claim 1 wherein the composition further comprises a high intensity sweetener selected from the group consisting of aspartame, acesulfame, alitame, brazien, cyclamic acid, dihydrochalcones, extract of *Dioscorophyllum cumminsii*, extract of the fruit of *Pentadiplandra brazzeana*, glycyrrhizin, hernandulcin, mogroside, monellin, neotame, neohesperidin, saccharin, sucralose, any of the glycosides of the aglycone Steviol including, but not limited to stevioside, rebaudioside A, rebaudioside B, rebaudioside C, rebaudioside D, rebaudioside E, rebaudioside F, dulcoside, rubusoside, steviolmonoside, steviolbioside, and 19-O-β glucopyranosol-steviol, thaumatin, extracts of sweet plants, such as *stevia* and luo han gou, and combinations thereof.

5. The method of claim 1 wherein the composition further comprises a flavor selected from cream, hazelnut, vanilla, chocolate, cinnamon, pecan, lemon, lime, raspberry, peach, mango, vanillin, butter, butterscotch, tea, orange, tangerine, caramel, strawberry, banana, grape, plum, cherry, blueberry, pineapple, elderberry, watermelon, bubble gum, cantaloupe, guava, kiwi, papaya, coconut, mint, spearmint, derivatives, and combinations thereof.

* * * * *